(12) United States Patent
Ryu et al.

(10) Patent No.: US 10,593,032 B2
(45) Date of Patent: Mar. 17, 2020

(54) DEFECT INSPECTION METHOD AND DEFECT INSPECTION APPARATUS

(71) Applicant: Samsung Electronics Co., Ltd., Suwon-si, Gyeonggi-do (KR)

(72) Inventors: Sung-Yoon Ryu, Suwon-Si (KR); Joon-Seo Song, Seoul (KR); Yu-Sin Yang, Seoul (KR); Chung-Sam Jun, Suwon-si (KR); Yun-Jung Jee, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 164 days.

(21) Appl. No.: 15/417,558

(22) Filed: Jan. 27, 2017

(65) Prior Publication Data

US 2018/0053295 A1 Feb. 22, 2018

(30) Foreign Application Priority Data

Aug. 17, 2016 (KR) .......................... 10-2016-0104096

(51) Int. Cl.
*G01N 21/95* (2006.01)
*G01N 21/88* (2006.01)
(Continued)

(52) U.S. Cl.
CPC ....... *G06T 7/0004* (2013.01); *G01N 21/8851* (2013.01); *G01N 21/9501* (2013.01); *G01N 21/956* (2013.01); *G01N 21/95607* (2013.01); *G01N 23/2251* (2013.01); *G02B 21/008* (2013.01); *G02B 21/0016* (2013.01); *G06T 7/11* (2017.01); *G06T 7/174* (2017.01); *H01J 37/22* (2013.01); *G01N 2021/8867* (2013.01); *G01N 2223/418* (2013.01); *G01N 2223/6116* (2013.01); *G02B 21/0036* (2013.01); *G06T 2207/10061* (2013.01);
(Continued)

(58) Field of Classification Search
CPC ......... G06T 7/0004; G06T 7/174; G06T 7/11; G06T 2207/20212; G06T 2207/10148; G06T 2207/10144; G06T 2207/10061; G06T 2207/30148; G02B 21/0036; G02B 21/008; G01N 21/956; G01N 23/2251; G01N 21/9501; G01N 2223/6116; G01N 2223/418; H01J 37/22; H01J 2237/24578
USPC ......................................................... 348/80
See application file for complete search history.

(56) References Cited

U.S. PATENT DOCUMENTS 7,796,804 B2  9/2010  Bhaskar et al.
8,126,258 B2  2/2012  Yang et al.
(Continued)

FOREIGN PATENT DOCUMENTS

KR   20080030800   4/2008
KR   100846633     7/2008
(Continued)

*Primary Examiner* — Susan E. Hodges
(74) *Attorney, Agent, or Firm* — Onello & Mello, LLP

(57) ABSTRACT

In a defect inspection method, first and second inspection conditions having a first sensitivity of detection signal and having a second sensitivity of a detection signal for a defect of interest (DOI), respectively, are determined. The first and second sensitivities are different. First and second images of the same detection region on a substrate surface under the first and second inspection conditions respectively, are obtained. The first and second images are matched to detect a defect in the detection region.

18 Claims, 9 Drawing Sheets

(51) Int. Cl.
- *G06K 9/00* (2006.01)
- *G01B 11/00* (2006.01)
- *G06T 7/00* (2017.01)
- *G01N 21/956* (2006.01)
- *H01L 21/66* (2006.01)
- *G02B 21/00* (2006.01)
- *G06T 7/11* (2017.01)
- *G06T 7/174* (2017.01)
- *G01N 23/2251* (2018.01)
- *H01J 37/22* (2006.01)

(52) U.S. Cl.
CPC ........... *G06T 2207/10144* (2013.01); *G06T 2207/10148* (2013.01); *G06T 2207/20212* (2013.01); *G06T 2207/30148* (2013.01); *H01J 2237/221* (2013.01); *H01J 2237/226* (2013.01); *H01J 2237/24578* (2013.01); *H01J 2237/28* (2013.01); *H01J 2237/2817* (2013.01)

(56) References Cited

U.S. PATENT DOCUMENTS

| | | | |
|---|---|---|---|
| 8,131,056 B2 | 3/2012 | Polonsky et al. | |
| 8,430,273 B2 | 4/2013 | Brouwer | |
| 9,040,937 B2 | 5/2015 | Yamaguchi et al. | |
| 9,092,846 B2 | 7/2015 | Wu et al. | |
| 2007/0230770 A1* | 10/2007 | Kulkarni | G06F 17/5045 382/149 |
| 2014/0219544 A1* | 8/2014 | Wu | G06T 7/001 382/149 |
| 2014/0354799 A1* | 12/2014 | Ojima | G01N 21/95607 348/126 |
| 2015/0332452 A1 | 11/2015 | Tsuchiya et al. | |
| 2016/0093465 A1* | 3/2016 | Nagano | H01J 37/222 250/307 |

FOREIGN PATENT DOCUMENTS

| | | |
|---|---|---|
| KR | 20080106889 | 12/2008 |
| KR | 20150113102 | 10/2015 |

\* cited by examiner

DEFECT INSPECTION METHOD AND DEFECT INSPECTION APPARATUS

PRIORITY STATEMENT

This application claims priority under 35 U.S.C. § 119 to Korean Patent Application No. 10-2016-0104096, filed on Aug. 17, 2016 in the Korean Intellectual Property Office (KIPO), the contents of which are herein incorporated by reference in their entirety.

BACKGROUND

1. Field

Example embodiments relate to a defect inspection method and a defect inspection apparatus. More particularly, example embodiments relate to a defect inspection method for detecting a defect of a pattern formed on a wafer. Example embodiments further relate to a defect inspection apparatus for performing the same.

2. Description of the Related Art

In semiconductor manufacturing, optical metrology is typically employed for measuring and evaluating properties such as optical properties, shapes of nano patterns, and the like, of nano samples. In particular, nano-samples can be measured and evaluated in real time in a nondestructive manner, for example, in a non-contact manner. In a conventional defect inspection algorithm, a reference image and an object image may be selected from images obtained from repetitive patterns. Such images may be compared with each other to determine whether or not a pattern is defective.

A magnitude of a defect detection signal may vary, for example according to the shape of a pattern adjacent to, or neighboring, a defect. The signal can further vary according to a defect depth, defect size, and the like. Accordingly, a detection signal for a defect of interest may be relatively weak due to the presence of noise in an adjacent pattern, or the presence of disturbance noise sourced from an underlying layer. As result, when the resulting reference image and the object image are compared with each other, signals related to noise variations such as pattern variations may be detected, while signals related to a defect of particular interest may not be detected.

SUMMARY

Example embodiments provide a high-precision defect inspection method.

Example embodiments provide a defect inspection apparatus for performing the above defect inspection method.

According to example embodiments, in a defect inspection method, first and second inspection conditions having a first sensitivity of detection signal and having a second sensitivity of a detection signal for a defect of interest (DOI), respectively, are determined. The first and second sensitivities are different. First and second images of the same detection region on a substrate surface under the first and second inspection conditions respectively, are obtained. The first and second images are matched to detect a defect in the detection region.

According to example embodiments, in a defect inspection method, a first image of a detection region on a substrate surface is obtained under a first inspection condition having a first sensitivity of a detection signal for a defect of interest (DOI). A second image of the same detection region is obtained under a second inspection condition having a second sensitivity of a detection signal for the DOI smaller than the first sensitivity. The first and second images are matched to detect a defect in the detection region.

According to example embodiments, in a defect inspection method, a first inspection signal is emitted on a detection region of a target substrate surface to be imaged resulting in a first detection signal of the detection region. A first image of the detection region is obtained under a first inspection condition by capturing the first detection signal of the detection region, the first inspection condition having a first sensitivity for a defect of interest of the target substrate surface so that a first detection signal value for the defect of interest has a first magnitude. A second inspection signal is emitted on the detection region of the target substrate surface to be imaged resulting in a second detection signal of the detection region. A second image of the detection region is obtained under a second inspection condition by capturing the second detection signal of the detection region, the second inspection condition having a second sensitivity for a defect of interest of the target substrate surface so that a second detection signal value for the defect of interest has a second magnitude. The first and second detection signal values of the defects of interest of the first and second images are compared to detect a defect in the detection region.

Accordingly, the first and second images may be obtained under the first and second inspection conditions having different sensitivities for the DOI at the same detection region and may be compared to detect a defect, to thereby prevent that when a reference image and an inspection image respectively obtained from different regions are compared, a signal for a defect of non-interest due to a pattern variation, discolor by location in wafer, an underlying structure, etc is detected. Further, multiple scanning operations may be employed to precisely detect a defect.

BRIEF DESCRIPTION OF THE DRAWINGS

Example embodiments of the present inventive concepts will be more clearly understood from the following detailed description taken in conjunction with the accompanying drawings. FIGS. 1 to 8C represent non-limiting, example embodiments as described herein.

FIG. 1 is a schematic view illustrating a defect inspection apparatus in accordance with example embodiments of the present inventive concepts.

FIG. 2 is a cross-sectional view illustrating an imaging unit of a defect inspection apparatus in accordance with some example embodiments of the present inventive concepts.

FIG. 3 is a cross-sectional view illustrating an imaging unit of a defect inspection apparatus in accordance with other example embodiments of the present inventive concepts.

FIG. 4 is a block diagram illustrating a controller of the defect inspection apparatus of FIG. 1 in accordance with example embodiments of the present inventive concepts.

FIG. 5 is a view illustrating multiple scanning of the defect inspection apparatus of FIG. 1 in accordance with example embodiments of the present inventive concepts.

FIG. 6 is a flow chart illustrating a defect inspection method in accordance with example embodiments in accordance with example embodiments of the present inventive concepts.

FIG. 8C is a view illustrating an image matched between the reference image and the first image in FIGS. 8A and 8B in accordance with example embodiments of the present inventive concepts.

DETAILED DESCRIPTION OF EMBODIMENTS

Figure 1:
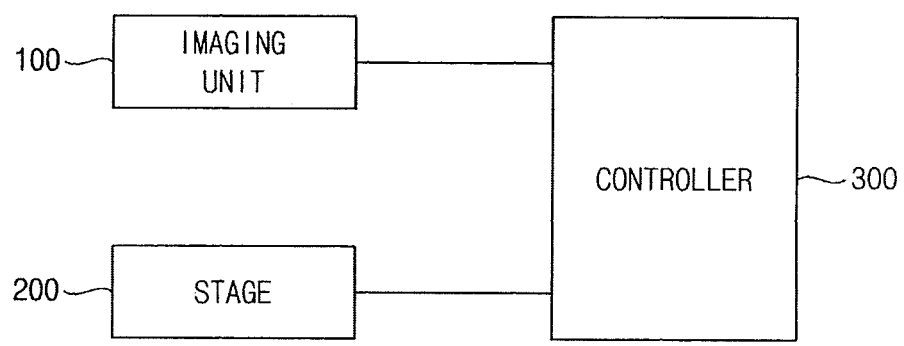
Figure 2:
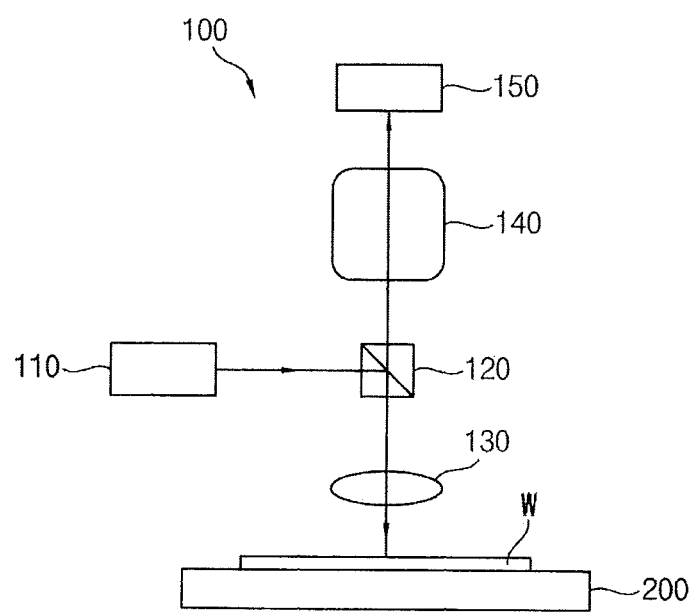
Figure 3:
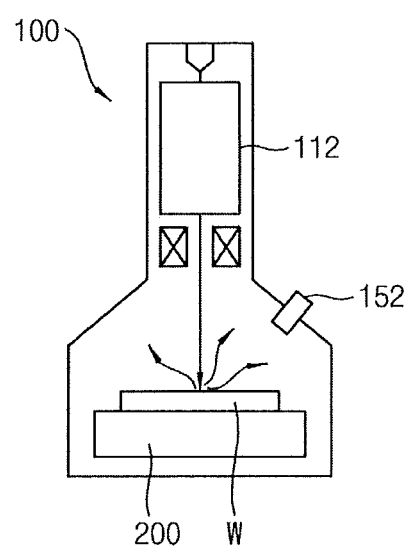
Figure 4:
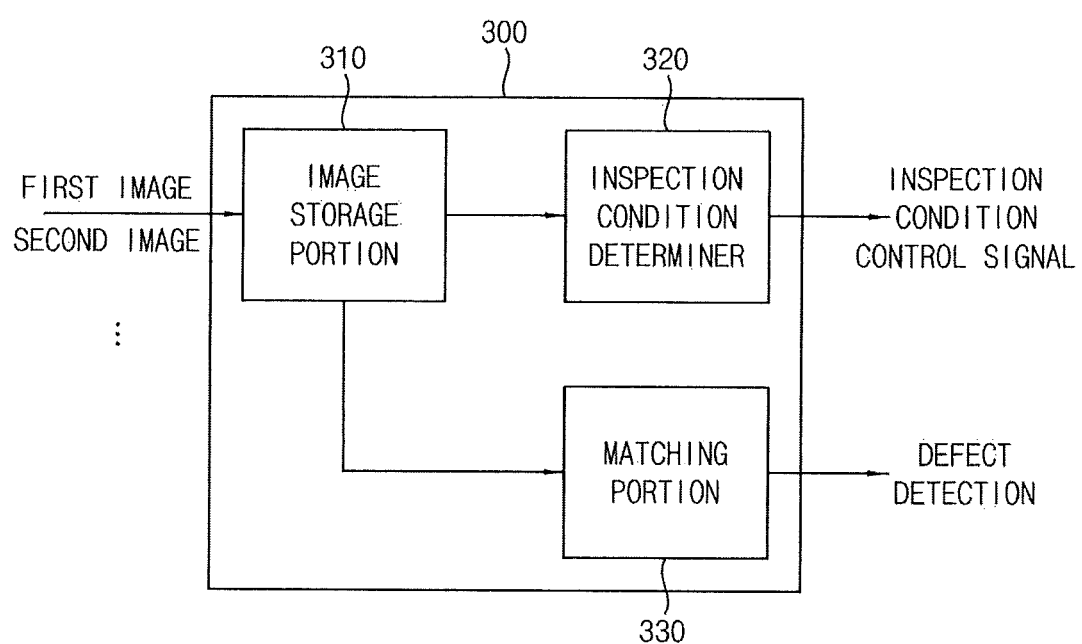
Figure 5:
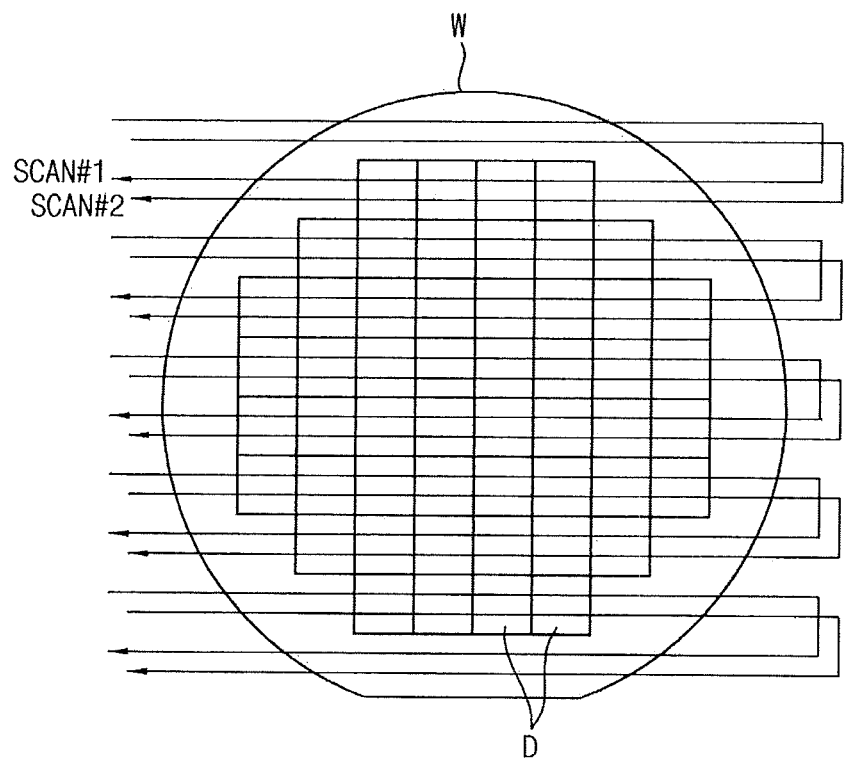

FIG. 1 is a view illustrating a defect inspection apparatus in accordance with example embodiments of the present inventive concepts. FIG. 2 is a cross-sectional view illustrating an imaging unit of a defect inspection apparatus in accordance with some example embodiments of the present inventive concepts. FIG. 3 is a cross-sectional view illustrating an imaging unit of a defect inspection apparatus in accordance with other example embodiments of the present inventive concepts. FIG. 4 is a block diagram illustrating a controller of the defect inspection apparatus in FIG. 1 in accordance with example embodiments of the present inventive concepts. FIG. 5 is a view illustrating multiple scanning of the defect inspection apparatus in FIG. 1 in accordance with example embodiments of the present inventive concepts.

Referring to FIGS. 1 to 5, a defect inspection apparatus 10 may include an imaging unit 100, a stage 200 and a controller 300.

In example embodiments, the defect inspection apparatus 10 may be used to detect a defect in a pattern formed on a wafer W in a nondestructive manner in a semiconductor manufacturing process for manufacturing semiconductor devices such as dynamic random access memory (DRAM) devices, vertical NAND (VNAND) devices, and other devices. This approach allows for in-line process monitoring of semiconductor processes performed on the semiconductor wafer W.

In some embodiments, a sample such as a semiconductor wafer W may be supported on the stage 200. The stage 200 may be caused to translate in front and rear directions, in left and right directions, in up and down directions and in clockwise and counterclockwise directions as driven by a driving mechanism (not illustrated). The driving mechanism may be connected to the controller 300, and may move the stage 200 in response to a control signal 201 input from the controller 300.

In some embodiments, the sample may take the form of a semiconductor wafer W including a multi-layered structure formed thereon. For example, the wafer W may refer to a substrate formed of a semiconductor or non-semiconductor material. The wafer may include one or more layers formed on the substrate. In various embodiments, such layers may include, but are not limited to, a resist layer, a dielectric material layer or a conductive material layer. As illustrated in FIG. 5, the wafer W may include repetitive patterns of a plurality of dies (chips) D which are separated by scribe lanes.

As illustrated in FIG. 2, in some example embodiments, the imaging unit 100 may include an optical microscope configured to irradiate a light beam onto the sample such as the semiconductor wafer W having patterns formed thereon. The imaging unit detects a reflected portion of the light beam to obtain an image of the pattern.

In some embodiments, the optical microscope may include an illumination source 110 such as a xenon (Xe) lamp. The light emitted from the xenon lamp may have a wavelength range of about 260 nm to about 400 m, or other wavelengths suitable for sample inspection. The illumination source 110 may be presented to a beam splitter 120 and the beam splitter 120 may be configured to reflect the light from the illumination source 110 to a refractive optical element 130. The refractive optical element 130 may be configured to focus the light from the beam splitter 120. The focused light is incident on the wafer W as an inspection signal. The illumination source 110, the beam splitter 120 and the refractive optical element 130 may form an illumination channel.

Incident light reflected from the wafer W may be collected by the refractive optical element 130 and may be directed through the beam splitter 120 and an optical system 140 to a detector 150. The refractive optical element 130, the beam splitter, 120, the optical system 140 and the detector 150 may form a detection channel. The light reflected from the wafer W may be detected through this detection channel to obtain an image. In some embodiments, the detector 150 may comprise an imaging detector such as a charge coupled device CCD, a CMOS device or an sCMOS device.

A pixel value (for example, a signal value of a signal-to-ratio (SNR)) of a signal detected at the same position of a surface of the wafer W may vary according to variations in optical conditions.

For example, the illumination source 110 may generate light energy at different wavelengths and/or different polarizations. In addition, the optical system 140 may further include additional components such as polarizing components, spatial filters, and the like. The signal value of the detection signal incident at the detector 150 provided from the light reflected from the wafer W may vary according to different wavelength bands, polarizations, apertures, focuses, etc. That is, the signal value of the detection signal at the same location on the wafer surface may vary according to certain predetermined optical conditions.

The optical conditions may be determined by the wavelength, the polarization, the aperture, the focus, etc. The optical microscope 100 may be connected to the controller 300, and may be made to scan using light of certain characteristics under an inspection condition such as an optical condition selected in response to a control signal input from the controller 300, in order to obtain the image of the pattern. As described herein, the optical microscope may be made to obtain multiple images of the same location (same detection region) of the wafer W as a result of multiple scanning operations, each under different, unique, inspection conditions.

As illustrated in FIG. 3, in other example embodiments, the imaging unit 100 may alternatively include an electron microscope configured to irradiate an electron beam onto a sample such as the semiconductor wafer W having a pattern formed thereon. In such a configuration, electrons emitting from the pattern are detected to obtain an image of the pattern.

The electron microscope may include an electron beam column 112 having an electron gun that generates a primary electron beam and an electron optical system for controlling a direction and a width of the primary electron beam and irradiating the electron beam onto the wafer W as an inspection signal. The electron microscope may further include a detector 152 for detecting electrons emitting from the wafer W as a detection signal.

For example, an acceleration voltage of the primary electron beam may be adjusted in accordance with a high voltage or low voltage to control a depth to which the electron beam penetrates into the sample. As the acceleration voltage of the electron beam is increased, the penetration depth of the electron beam may be increased, and thus, an amount of electrons emitting from the wafer (W) may be increased and a signal value of a detection signal obtained from the electrons emitting from the wafer (W) may be varied. That is, the signal value of the detection signal at the same location on the wafer surface may vary according to a predetermined electron beam condition.

The electron beam condition may be determined by a number of factors, including the acceleration voltage of the electron beam, a polarization of the beam, an aperture of the electron beam column, etc. The electron microscope may be connected to the controller 300, and may scan with an electron beam under an inspection condition such as the electron beam condition in response to a control signal input from the controller 300 to obtain the image of the pattern on the wafer W. As described herein, the electron microscope may be made to obtain multiple images of the same location (same detection region) of the wafer W, as a result of multiple scanning operations, each under different, unique, inspection conditions.

As illustrated in FIG. 4, the controller may include an image storage portion 310, an inspection condition determiner 320 and a matching portion 330. In some embodiments, the controller 300 may determine an inspection condition of the imaging unit 100 and detect a defect of a detection region from obtained images.

In particular, the image storage portion 310 may store images input from the detector of the imaging unit 100. The image storage portion 310 may receive and store a plurality of images of the same detection region on a surface of the wafer W which are obtained, respectively, under different inspection conditions. Each of the images may include detection signal values for a defect of interest (DOI). Additionally, in some embodiments, the image storage portion 310 may receive a design image for the pattern formed on the wafer W. For example, the design image may include a graphic data system (GDS) image stored in a layout format.

The inspection condition determiner 320 may select first and second inspection conditions from the images. In some cases a difference value between detection signal values for the DOI obtained under the first and second inspection conditions may be determined to be a significant value.

The difference value between the detection signal values for the DOI of a corresponding same location of the obtained images may be calculated. Then, different conditions under which the difference value between the detection signal values is equal to or greater than a significant value may be selected as the first and second inspection conditions.

For example, the detection signal value for the DOI of the image obtained under the first inspection condition may be relatively great, for example, the maximum value, and the detection signal value for the DOI of the image obtained under the second inspection condition may be relatively small, for example, the minimum value. That is, a sensitivity for the DOI under the first inspection condition may be relatively good, for example, at the top of the sensitivity range, and a sensitivity for the DOI under the second inspection condition may be relatively poor, for example, at the bottom of the sensitivity range.

Additionally, under some conditions, the difference value between the detection signal values, for example the for the defect of interest (DOI) under the first and second inspection conditions may be greater than a difference value between detection signal values for a defect of non-interest under the first and second inspection conditions.

The inspection condition determiner 320 may output the determined inspection condition as an inspection condition control signal to the imaging unit 100. The imaging unit 100 may obtain an image of the pattern under the determined inspection condition in response to the control signal of the inspection condition determiner 320. For example, the imaging unit 100 may obtain first and second images of the same detection region through multiple scanning operations under the first and second inspection conditions respectively.

The matching portion 330 may match the images to detect a defect in the detection region.

In particular, the matching portion 330 may match the first and second images of the same detection region respectively obtained under the first and second inspection conditions, to detect a defect in the detection region. The matching portion 330 may calculate a difference between detection signal values, for example, pixel values, of a corresponding location of the first and second images. For example, the detection signal value may include a signal value of a signal-to-noise ratio (SNR).

In example embodiments, the controller 300 may control the imaging unit 100 and the stage 200 to perform the multiple scanning operations on the wafer W using different inspection conditions. As illustrated in FIG. 5, in the multiple scanning, a first scanning (scan #1) having scanning of right direction, moving of vertical direction and scanning of left direction under the first inspection condition may be performed on the same inspection region to obtain the first image. Then, a second scanning (scan #2) having scanning of right direction, moving of vertical direction and scanning of left direction under the second inspection condition may be performed on the same inspection region repeatedly to obtain the second image. Thus, in this manner, the first and second images may be sequentially obtained. In various embodiments, the various techniques for performing the multiple scanning operation are not limited thereto, and various image scanning approaches may be performed to achieve the desired multiple scanning operation.

Alternatively, the imaging unit may include two independent imaging mechanisms and may obtain first and second images, contemporaneously, at the same time, through a single scanning by each of the two imaging mechanisms configured under the first and second inspection conditions. For example, the imaging unit may include a first imaging mechanism configured to obtain an image of the same detection region of the wafer W using an optical microscope and a second imaging mechanism configured to obtain an image of the same detection region of the wafer W using an electron microscope. In this case, the first and second inspection conditions may be determined by the imaging mechanism. That is, the image obtained by the first imaging mechanism may be a first image obtained under a first inspection condition, and the image obtained by the second imaging mechanism may be a second image obtained under a second inspection condition. In other embodiments, the first and second imaging mechanisms can both employ optical microscopes. In other embodiments, the first and second imaging mechanisms can both employ electron microscopes.

As described above, the defect inspection apparatus may change optical conditions at a detection region of the defect of interest (DOI) to obtain detection signals and analyze the detection signals to select optical inspection conditions where a difference value between the detection signal values for only DOI is equal to or greater than a significant value while a difference value between the detection signal values for a defect of non-interest (that is, a detection signal generated due to a pattern variation, an underlying defect, etc, other than a defect of interest), is not significant. A first scanning inspection with a first optical inspection condition where a sensitivity of the detection signal value for the DOI is relatively good may be performed to obtain a first inspection image, and a second scanning inspection with a second optical inspection condition where a sensitivity of the detection signal value for the DOI is relatively poor may be performed to obtain a second inspection image. Then, through a comparison of the first and second inspection images, undesired detection signals such as the pattern variation, the underlying defect, etc. may be eliminated and only desired detection signals for the DOI may be maintained or amplified to more precisely inspect a defect.

Hereinafter, a method of inspecting a defect of a pattern formed on a wafer using the defect inspection apparatus will be explained.

Figure 6:
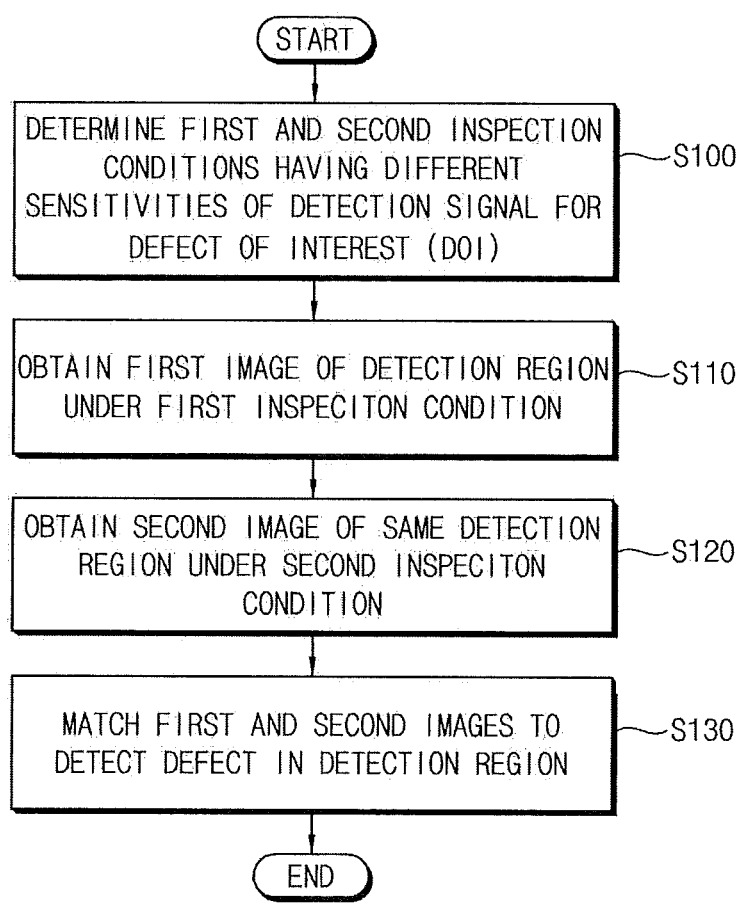
Figure 7A:
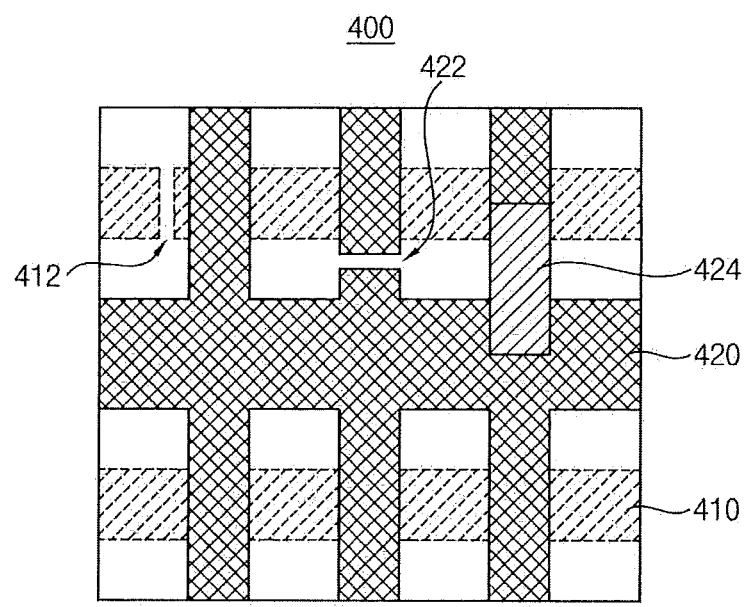
FIGS. 7A and 7B are views illustrating first and second images of the same detection region of a wafer respectively obtained under first and second inspection conditions in accordance with example embodiments of the present inventive concepts.
Figure 7B:
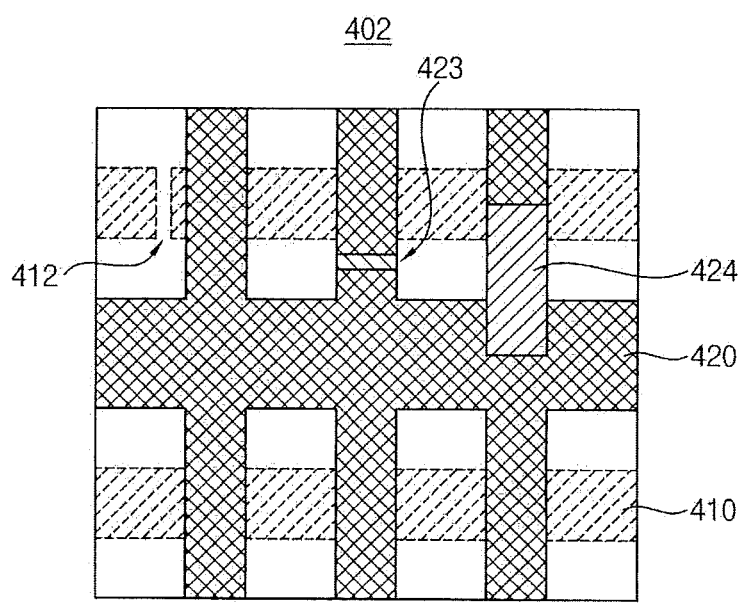
Figure 7C:
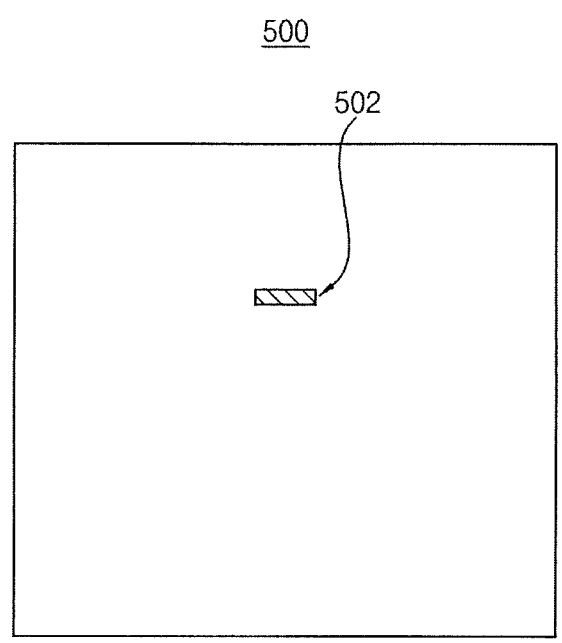
FIG. 7C is a view illustrating an image matched between the first and second images in FIGS. 7A and 7B in accordance with example embodiments of the present inventive concepts.
Figure 8A:
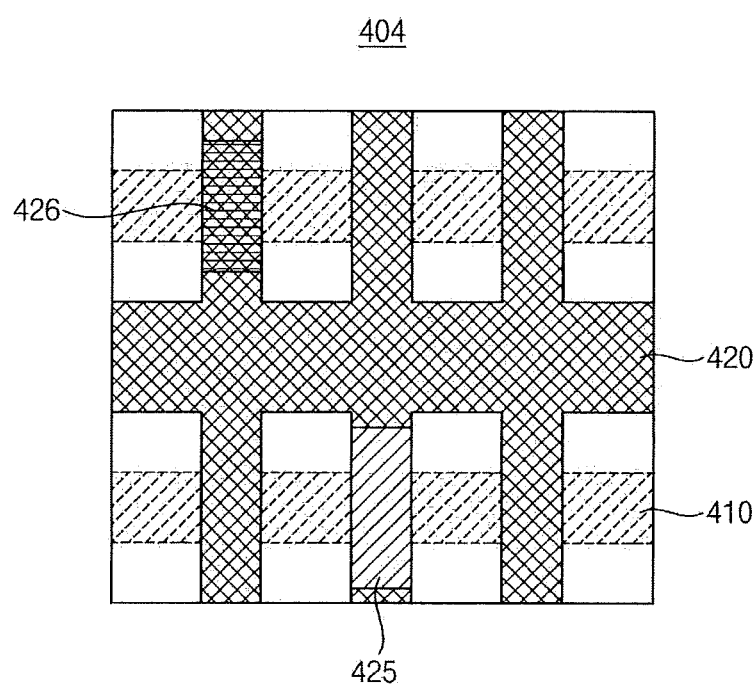
FIGS. 8A and 8B are views illustrating a reference image of a die region adjacent to the detection region of the wafer and the first image of the detection region of the wafer in accordance with comparative example embodiments of the present inventive concepts.
Figure 8B:
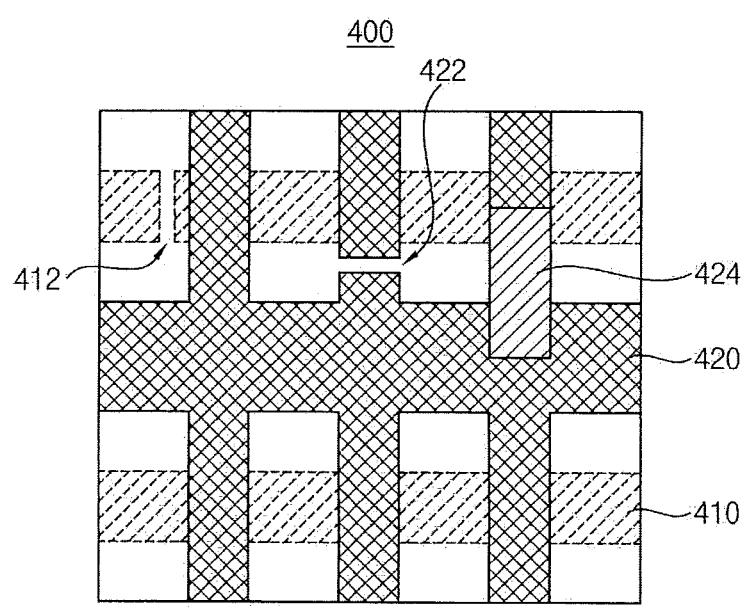
Figure 8C:
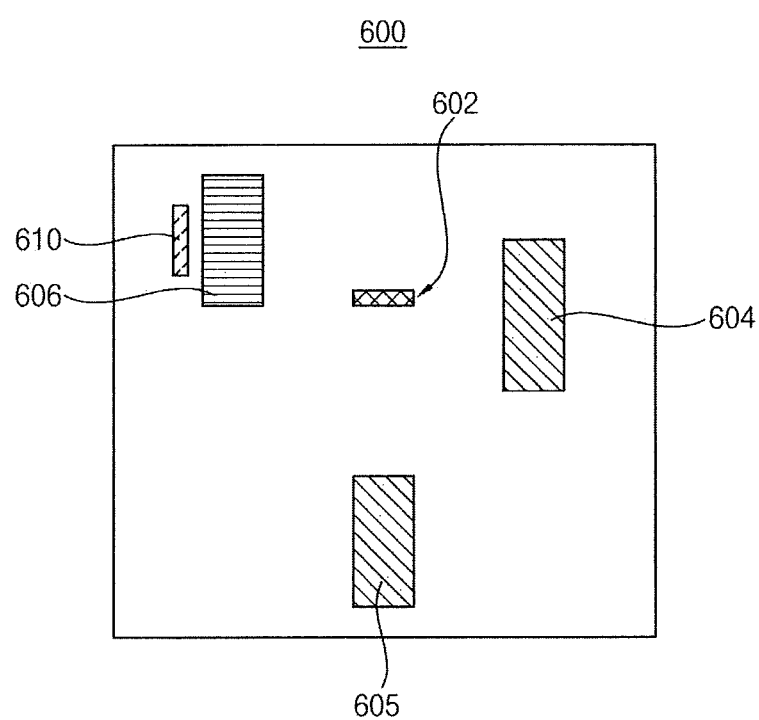

FIG. 6 is a flow chart illustrating a defect inspection method in accordance with example embodiments of the present inventive concepts. FIGS. 7A and 7B are views illustrating first and second images of the same detection region of a wafer respectively obtained under first and second inspection conditions in accordance with example embodiments of the present inventive concepts. FIG. 7C is a view illustrating an image matched between the first and second images in FIGS. 7A and 7B. FIGS. 8A and 8B are views illustrating a reference image of a die region adjacent to the detection region of the wafer and the first image of the detection region of the wafer in accordance with comparative example embodiments. FIG. 8C is a view illustrating an image matched between the reference image and the first image in FIGS. 8A and 8B.

Referring to FIGS. 1 and 6, first and second inspection conditions having different sensitivities of a detection signal for a defect of interest (DOI) may be determined (S100).

In example embodiments, an imaging unit 100 may scan a wafer W repeatedly under a plurality of inspection conditions to obtain a plurality of images of the same detection region.

A difference between detection signals for the DOI of the obtained images at a corresponding same location may be calculated, and then, different conditions under which the difference value between the detection signal values is equal to or greater than a significant value may be selected as first and second inspection conditions. For example, the detection signal value for the DOI of the image obtained under the first inspection condition may be relatively great, for example, the maximum value, and the detection signal value for the DOI of the image obtained under the second inspection condition may be relatively small, for example, the minimum value. A sensitivity for the DOI under the first inspection condition may be relatively good, for example, the top of the sensitivity range, and a sensitivity for the DOI under the second inspection condition may be relatively poor, for example, the bottom of the sensitivity range. The difference value between the detection signal values for the DOI under the first and second inspection conditions may be greater than a difference value between detection signal values for a defect of non-interest under the first and second inspection conditions.

Then, first and second images of the same detection region of the wafer may be obtained under the first and second inspection conditions respectively (S110, S120), and then, the first and second images may be matched to detect a defect in the detection region (S130). In some embodiments, the first and second images may be captured contemporaneously, by first and second imaging mechanisms contemporaneously inspecting the same inspection region of the sample, as described herein.

In example embodiments, the first and second images of the same detection region may be obtained through multiple scanning with the first and second inspection conditions respectively. Then, a difference between detection signal values, for example, pixel values, of a corresponding location of the first and second images may be calculated. For example, the detection signal value may include a signal value of a signal-to-noise ratio (SNR).

As illustrated in FIG. 7A, a first image 400 may be an inspection image of a detection region of a wafer obtained under a first inspection condition. The first image 400 may include an image 410 of a lower pattern and an image 420 of an upper pattern. The image 410 of the lower pattern may have a defective portion 412 due to a defect of the lower pattern. The pattern 420 of the upper pattern may have a defective portion 422 due to a defect of the upper pattern and a defective portion 424 due to a pattern variation. Here, the defective portion 422 due to the defect of the upper pattern may be a defect of interest, while the defective portion 412 due to the defect of the lower pattern and the defective portion 424 due to the pattern variation may be defects of non-interest.

As illustrated in FIG. 7B, a second image 402 may be an inspection image of the same detection region of the wafer obtained under a second inspection condition. The second image 402 may include an image 410 of a lower pattern and an image 420 of an upper pattern. The image 410 of the lower pattern may have a defective portion 412 due to a defect of the lower pattern. The pattern 420 of the upper pattern may have a defective portion 423 due to a defect of the upper pattern and a defective portion 424 due to a pattern variation. Here, the defective portion 423 due to the defect of the upper pattern may be a defect of interest, and the defective portion 412 due to the defect of the lower pattern and the defective portion 424 due to the pattern variation may be defects of non-interest.

A detection signal value (pixel value) for the defective portion 422 due to the upper pattern of the image 400 obtained under the first inspection condition may be greater than a detection signal value (pixel value) for the defective portion 423 due to the upper pattern of the image 402 obtained under the second inspection condition. Detection signal values for the defective portion 412 due to the defect of the lower pattern and the defective signal values for the defective portion 424 due to the pattern variation of the first image 400 obtained under the first inspection condition may be substantially the same as detection signal values for the defective portion 412 due to the defect of the lower pattern and the defective signal values for the defective portion 424 due to the pattern variation of the second image 402 obtained under the second inspection condition.

As illustrated in FIG. 7C, the first image 400 and the second image 402 may be matched each other to detect a defective portion 502 corresponding to a defect of interest (DOI). Here, the second image 402 having a relatively small signal value for the defect of interest (DOI) may be used as a reference image, the first image 400 having a relatively large signal value for the defect of interest (DOI) may be used as an inspection image, and the reference image and the inspection image may be spatially matched and compared to each other to detect the defective portion 502 corresponding to the defect of interest (DOI).

Hereinafter, a defect inspection method in accordance with comparative example embodiments where an image of a die (or cell) region adjacent to the detection region of the wafer is used as a reference image will be explained.

As illustrated in FIG. 8A, a third image 404 may be an image of a die region adjacent to the detection region of the wafer obtained under a first inspection condition. The third image 404 may include an image 410 of a lower pattern and an image 420 of an upper pattern. The pattern 420 of the upper pattern may have defective portions 425 and 426 due to pattern variations. Here, the defective portions 425 and 426 due to the pattern variations may considered to be defects of non-interest. Since the third image 404 of the die region adjacent to the detection region has no defective portion corresponding to a defect of interest, the third image 404 may be used as a reference image.

As illustrated in FIG. 8B, a first image 400 may be an inspection image of the detection region of the wafer obtained under the first inspection condition. The first image 400 may include an image 410 of a lower pattern and an image 420 of an upper pattern. The image 410 of the lower pattern may have a defective portion 412 due to a defect of the lower pattern. The pattern 420 of the upper pattern may have a defective portion 422 due to a defect of the upper pattern and a defective portion 424 due to a pattern variation. Here, the defective portion 422 due to the defect of the upper pattern may be a defect of interest (DOI), and the defective portion 412 due to the defect of the lower pattern and the defective portion 424 due to the pattern variation may be defects of non-interest.

In some embodiments, the first and third images 400 and 404 may be obtained through a single scanning by the imaging unit 100.

As illustrated in FIG. 8C, the reference image 404 and the first image 400 may be spatially matched and compared with each other to obtain a matching image 600. In the matching image 600, a defective portion 602 of a defect of interest as well as defective portions 604, 605, 606 and 610 of defects of non-interest may be detected as defects. Since the reference image 404 and the first image 400 have defective portions due to the pattern variation and the lower pattern (defects of non-interest) at different positions, when the reference image 404 and the first image 400 are matched to each other and compared, the defects of non-interest may be inadvertently detected as defects.

In the defect inspection method in accordance with comparative example embodiments, when the portions due to defects other than defects of interest (DOI) present in the reference image 404 and the first image 400 have the same detection signal values, the portions having the same detection signal values may not be detected as defects. However, in an actual wafer, the defects of non-interest due to the pattern variation, discolor by location in wafer, an underlying structure, etc, may be detected as defects.

On the other hand, the first and second images 400 and 402 of the illustrative example of FIGS. 7A-7C may be obtained under the first and second optical conditions under which detection sensitivities for the defect of interest (DOI) are different from each other but, at the same time, detection sensitivities for defects of non-interest are similar to or the same as each other. Accordingly, the first and second images 400 and 402 may be matched and compared to precisely detect a defect of interest (DOI).

As mentioned herein, in the defect inspection method in accordance with embodiments of the present inventive concepts, first and second inspection conditions having different sensitivities of a detection signal for a defect of interest (DOI) may be determined, first and second images of the same detection region of a wafer may be obtained under the first and second inspection conditions respectively, and then, the first and second images may be matched and compared to detect a defect in the detection region.

Accordingly, when a reference image and an inspection image obtained from different regions are compared, inadvertent and undesired detection of a signal indicating a defect of non-interest due to a pattern variation, discolor by location in wafer, an underlying structure, etc., may be prevented.

The methods described herein are applicable to the manufacture a semiconductor device such as a logic device or a memory device. For example, the semiconductor device may include logic devices such as central processing units (CPUs), main processing units (MPUs), application processors (APs), etc., volatile memory devices such as DRAM devices, SRAM devices, etc., or non-volatile memory devices such as flash memory devices, PRAM devices, MRAM devices, RRAM devices, etc.

The foregoing is illustrative of example embodiments and is not to be construed as limiting thereof. Although a few example embodiments have been described, those skilled in the art will readily appreciate that many modifications are possible in example embodiments without materially departing from the novel teachings and advantages of the present invention. Accordingly, all such modifications are intended to be included within the scope of example embodiments as defined in the claims.

What is claimed is:

1. A defect inspection method, comprising:
    determining first and second inspection conditions having a first sensitivity of detection signal and having a second sensitivity of a detection signal for a defect of interest (DOI), respectively, the first sensitivity being greater than the second sensitivity;
    obtaining first and second inspection images of a same detection region on a substrate surface under the first and second inspection conditions respectively, by scanning the substrate surface with a light or an electron beam, wherein the first inspection image has a first signal value for the DOI and the second inspection image has a second signal value for the DOI, the first signal value being greater than the second signal value;
    determining the first inspection image as an object image and determining the second inspection image as a reference image; and
    detecting a defect in the detection region by matching the object image and the reference image to each other to calculate a difference between detection signal values of a corresponding location of the first and second inspection images,
    wherein determining the first and second inspection conditions comprises:
    obtaining a plurality of images for the DOI under different inspection conditions; and
    selecting different conditions under which a difference value between detection signal values for the DOI is equal to or greater than a significant value, as the first and second inspection conditions, and wherein the first and second inspection images are for the DOI on a same substrate.

2. The method of claim 1, wherein the detection signal comprises a signal-to-noise ratio (SNR) signal.

3. The method of claim 1, wherein a difference value between detection signal values for the DOI under the first and second inspection conditions is greater than a difference value between detection signal values for a defect of non-interest under the first and second inspection conditions.

4. The method of claim 1, wherein obtaining the first and second inspection images comprises scanning the substrate surface with light energy using an optical microscope.

5. The method of claim 1, wherein obtaining the first and second inspection images comprises scanning the substrate surface with the electron beam using an electron microscope.

6. The method of claim 1, wherein obtaining the first and second inspection images comprises obtaining the first and second inspection images at the same time.

7. The method of claim 1, wherein the first and second inspection conditions are defined by at least one of a wavelength band, focus, aperture, polarization, imaging mechanism or acceleration voltage of the electron beam.

8. The method of claim 1, wherein matching the first and second inspection images comprises calculating a difference value between detection signal values for the DOI of a corresponding same location of the first and second inspection images.

9. A defect inspection method, comprising:
obtaining a first inspection image of a detection region on a substrate surface under a first inspection condition having a first sensitivity of a detection signal for a defect of interest (DOI);
obtaining a second inspection image of the same detection region under a second inspection condition having a second sensitivity of a detection signal for the DOI smaller than the first sensitivity;
matching the first and second inspection images to each other to calculate a difference between detection signal values of a corresponding location of the first and second inspection images to detect a defect in the detection region; and
selecting different conditions under which a difference value between detection signal values for the DOI is equal to or greater than a significant value, as the first and second inspection conditions,
wherein obtaining the first and second inspection images comprises scanning the substrate surface with a light or an electron beam,
wherein the first and second inspection images are for the DOI on a same substrate, and
wherein matching the first and second inspection images to each other comprises:
using the first inspection image as an object image and using the second inspection image as a reference image; and
matching the object image and the reference image to detect the defect.

10. The method of claim 9, wherein a detection signal value for the DOI under the first inspection condition is greater than a detection signal value for the DOI under the second inspection condition.

11. The method of claim 9, wherein the first and second inspection conditions are defined by at least one of a wavelength band, focus, aperture, polarization, imaging mechanism and acceleration voltage of the electron beam.

12. A defect inspection method comprising:
emitting a first inspection signal on a detection region of a target substrate surface to be imaged resulting in a first detection signal of the detection region, and obtaining a first inspection image of the detection region under a first inspection condition by capturing the first detection signal of the detection region, selecting the first inspection condition to have a first sensitivity for a defect of interest of the target substrate surface so that a first detection signal value for the defect of interest has a first magnitude;
emitting a second inspection signal on the detection region of the target substrate surface to be imaged resulting in a second detection signal of the detection region, and obtaining a second inspection image of the detection region under a second inspection condition by capturing the second detection signal of the detection region, selecting the second inspection condition to have a second sensitivity for a defect of interest of the target substrate surface so that a second detection signal value for the defect of interest has a second magnitude smaller than the first magnitude;
determining the first inspection image as an object image and determining the second inspection image as a reference image; and
detecting a defect in the detection region by matching the object image and the reference image to each other to calculate a difference value between the first and second detection signal values,
wherein the difference value between the first and second detection signal values for the defect of interest under the first and second inspection conditions is greater than a difference value between detection signal values for a defect of non-interest under the first and second inspection conditions,
wherein the first and second inspection signals are light energy signals, or wherein the first and second inspection signals are electron beams, and
wherein the first and second inspection images are for the defect of interest on a same substrate.

13. The defect inspection method of claim 12, wherein obtaining the first and second inspection images of the detection region comprises obtaining the first and second inspection_images contemporaneously.

14. The method of claim 1, wherein obtaining the first and second inspection images comprises using both an optical microscope and an electron microscope.

15. The method of claim 1, wherein obtaining the first and second inspection images comprises obtaining the first and second inspection images sequentially.

16. The method of claim 9, wherein obtaining the first and second inspection images comprises using both an optical microscope and an electron microscope.

17. The defect inspection method of claim 12, wherein obtaining the first and second inspection images comprises using both an optical microscope and an electron microscope.

18. The defect inspection method of claim 12, wherein obtaining the first and second inspection images of the detection region comprises obtaining the first and second images sequentially.

* * * * *